(12) United States Patent
Kolve et al.

(10) Patent No.: US 8,241,563 B2
(45) Date of Patent: Aug. 14, 2012

(54) AIR SANITIZATION SYSTEM WITH FIBER OPTIC MONITORING SYSTEM

(75) Inventors: Michael P. Kolve, Saint Charles, MO (US); Nathan W. Provance, Saint Ann, MO (US); Dennis L. Wagner, Manchester, MO (US)

(73) Assignee: Hussmann Corporation, Bridgeton, MO (US)

( * ) Notice: Subject to any disclaimer, the term of this patent is extended or adjusted under 35 U.S.C. 154(b) by 473 days.

(21) Appl. No.: 12/615,350

(22) Filed: Nov. 10, 2009

(65) Prior Publication Data

US 2011/0110814 A1    May 12, 2011

(51) Int. Cl.
*A61L 9/00* (2006.01)
*A61L 2/00* (2006.01)
*A62B 7/08* (2006.01)
*B01L 1/04* (2006.01)
*C01B 13/10* (2006.01)

(52) U.S. Cl. ........... 422/5; 422/1; 422/3; 422/4; 422/22; 422/24; 422/28; 422/108; 422/119; 422/121; 422/124; 422/186.07; 422/186.3; 422/305; 422/900; 250/214 R; 250/492.1; 250/505.1; 204/176; 424/187; 219/121.57; 73/DIG. 11

(58) Field of Classification Search ............... 422/1, 3–5, 422/22, 24, 28, 108, 119, 121, 124, 186.07, 422/186.3, 305, 900; 250/214 R, 492.1, 250/505.1; 204/176; 454/187; 219/121.57; 73/DIG. 11

See application file for complete search history.

(56) References Cited

U.S. PATENT DOCUMENTS

| 4,349,511 | A | 9/1982 | Owen |
| 5,503,808 | A | 4/1996 | Garbutt et al. |
| 6,053,968 | A | 4/2000 | Miller |
| 6,063,169 | A | 5/2000 | Cramer et al. |
| 6,726,885 | B2 | 4/2004 | Borgstrom |
| 7,350,371 | B2 | 4/2008 | Lee et al. |
| 2002/0127442 | A1 | 9/2002 | Connor et al. |
| 2004/0175288 | A1 | 9/2004 | Horton, III |
| 2007/0170123 | A1 | 7/2007 | Phillips et al. |
| 2007/0217987 | A1 | 9/2007 | Belanger et al. |
| 2008/0274012 | A1* | 11/2008 | Cumberland et al. ............ 422/4 |

OTHER PUBLICATIONS

S. O'Keeffe, G. Dooly, C. Fitzpatrick, E. Lewis, Optical Fibre Sensors Research Group, Department of Electronic and Computer Engineering, University of Limerick, Ireland, "Optical fibre sensor for the measurement of ozone," Journal of Physics: Conference Series 15, 2005, pp. 213-218, Institute of Physics Publishing.

* cited by examiner

*Primary Examiner* — Jill Warden
*Assistant Examiner* — Monzer Chorbaji
(74) *Attorney, Agent, or Firm* — Michael Best & Friedrich LLP

(57) ABSTRACT

An air sanitization system including a housing having an inlet and an outlet, an ozone generator disposed in the housing and positioned between the inlet and outlet, at least one fiber optic cable positioned in visible proximity to the ozone generator, a visible light detector, and a controller. The housing is configured to receive a flow of an oxygen-containing gas through the inlet, and the ozone generator generates ozone from the flow of oxygen-containing gas. The at least one fiber optic cable is configured to receive and transmit visible light from the ozone generator. The visible light detector detects an amount of visible light transmitted by the at least one fiber optic cable. The controller is in communication with the visible light detector for determining whether the amount of visible light transmitted by the at least one fiber optic cable corresponds to a failure of the ozone generator.

21 Claims, 5 Drawing Sheets

AIR SANITIZATION SYSTEM WITH FIBER OPTIC MONITORING SYSTEM

BACKGROUND

The present invention relates to ozone generators for air sanitization and control systems for controlling the operation of ozone generators.

SUMMARY

In one embodiment, the invention provides an air sanitization system having a housing having an inlet and an outlet, an ozone generator disposed in the housing and positioned between the inlet and outlet, at least one fiber optic cable positioned in visible proximity to the ozone generator, a visible light detector, and a controller. The housing is configured to receive a flow of an oxygen-containing gas through the inlet, and the ozone generator generates ozone from the flow of oxygen-containing gas. The at least one fiber optic cable is configured to receive and transmit visible light from the ozone generator. The visible light detector detects an amount of visible light transmitted by the at least one fiber optic cable. The controller is in communication with the visible light detector for determining whether the amount of visible light transmitted by the at least one fiber optic cable corresponds to a failure of the ozone generator.

In another embodiment the invention provides a method of controlling an air sanitization system. The method includes generating ozone with an ozone generator, detecting visible light to determine failure of the ozone generator, and ceasing operation of the ozone generator when a predetermined level of visible light corresponding to failure of the ozone generator is detected.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
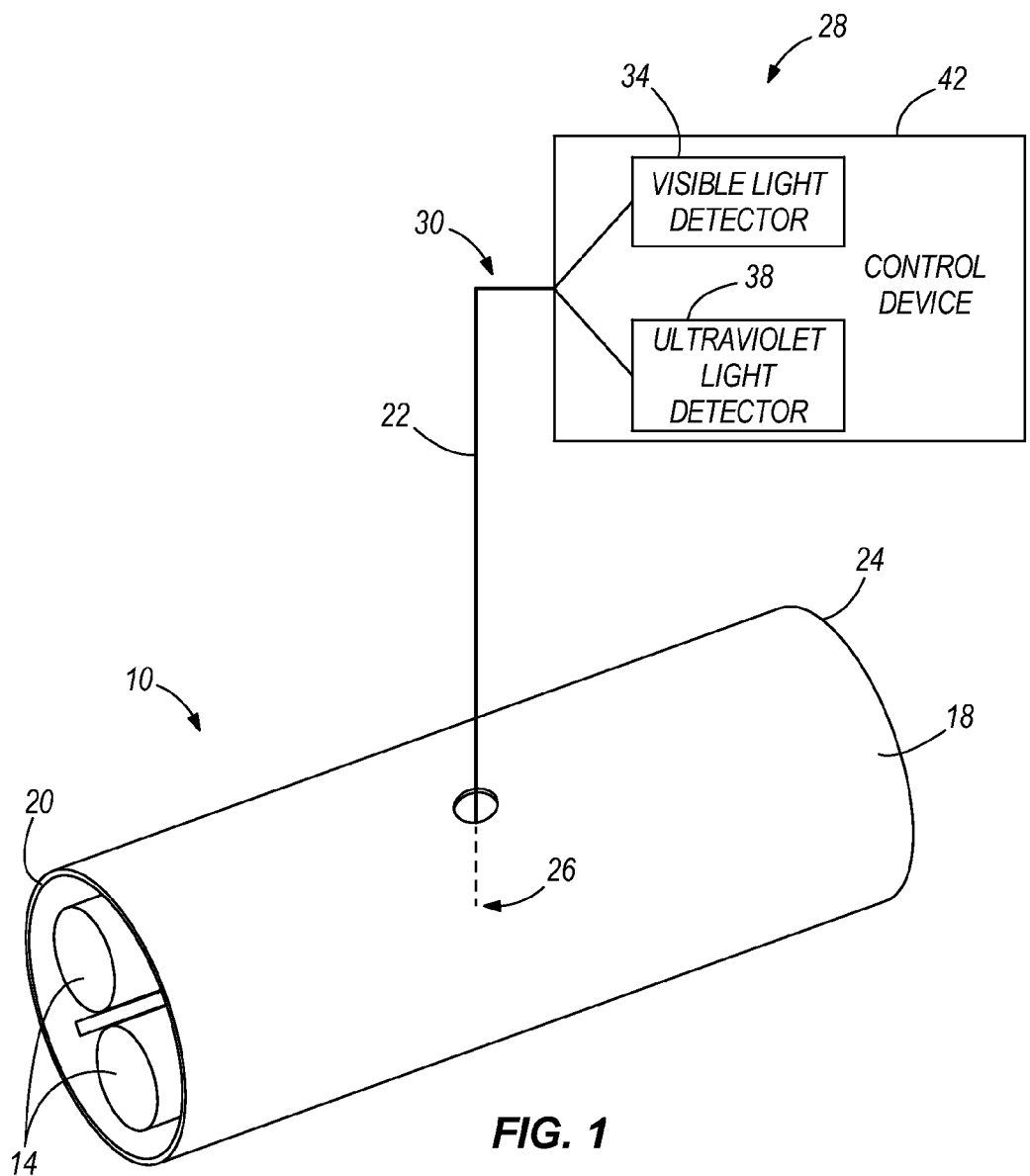
FIG. 1 is a schematic view of an ozone generator having a fiber optic detection system according to a first construction of the invention.

FIG. 1 illustrates an ozone generation system 10 having a two-tube glass array of reactive oxygen species (ROS) generators 14 housed in a housing 18. Reactive oxygen species include one or more of oxygen ions, free radicals, organic and inorganic peroxides, ozone, and other reactive oxygen species. These reactive oxygen species oxidize pollutants to effectively remove them from the air and surfaces. The housing 18 has an inlet 20 for receiving an oxygen-containing gas and an outlet 24 for expelling an ROS-containing air. The ROS generators 14 are positioned between the inlet 20 and outlet 24. One example of an ozone generation system having arrays of glass tube ROS generators, and suitable for use with the present invention, is disclosed in currently pending U.S. Patent Application Publication No. 2007/0119699, filed Nov. 30, 2005, which is fully incorporated by reference herein. In other constructions, the ozone generation system 10 may have arrays of one, three or more ROS generators 14.

A control system 28 monitors the ozone generation system 10 and controls the operation thereof. The control system 28 includes a fiber optic cable 22, a visible light detector 34, an ultraviolet light detector 38, and a controller 42.

The fiber optic cable 22 receives and transmits light emitted by the ROS generators 14. The fiber optic cable 22 includes a plastic optical fiber (POF) having a standard polyethylene jacket, a fluorinated polymer cladding and a plastic polymethyl methacrylate (PMMA) core. Light received at one end of the jacketed POF fiber optic cable 22 is transmitted to an opposite end of the fiber optic cable 22. In other constructions, other types of fiber optic cable suitable for receiving and transmitting light may be employed.

The fiber optic cable 22 is positioned having a first end 26 inside the housing 18 and within visible proximity of the ROS generators 14 (e.g., positioned to receive light emitted by the ROS generators 14). A second end 30 of the fiber optic cable 22 is positioned proximate the visible light detector 34. The visible light detector 34 is positioned to receive the light transmitted by the fiber optic cable 22. The ultraviolet light detector 38 is also positioned proximate the second end 30 of the fiber optic cable 22 to receive the light. In other constructions, two separate fiber optic cables 22 may be employed— one separate fiber optic cable for each of the visible light detector 34 and the ultraviolet light detector 38, similar to the construction illustrated in FIG. 4, which will be described in greater detail below.

The controller 42 is in communication with the visible light detector 34 and the ultraviolet light detector 38 for receiving a signal therefrom corresponding to the intensity of visible light emitted by the ROS generators 14 and the wavelength of ultraviolet light emitted by the ROS generators 14, respectively. The signals may be digital or analog. The controller 42 is operable to cease operation of the ozone generation system 10 in response to the signal received.

The ROS generators 14 emit visible light during operation. If the glass of the ROS generator cracks or fails, high energy visible light will be emitted. The controller 42 is programmed to determine whether the signal provided by the visible light detector 34 corresponds to a level of light emitted by a cracked or failed glass ROS generator 14 tube. If the controller 42 determines that the ROS generator 14 has cracked or failed, the controller 42 shuts off the ozone generation system 10.

To determine a concentration of ozone generated by the ROS generators 14, the ultraviolet light detector 38 detects the optical absorption of ultraviolet light between 230 nanometers (nm) and 270 nm. In a preferred construction, the ultraviolet light detector 38 detects the optical absorption of ultraviolet light at approximately 254 nm, the fundamental absorption wavelength of ozone. The controller 42 is programmed to determine whether the signal provided by the ultraviolet light detector is indicative of an ozone concentration that is predetermined to be too high. If the controller 42 determines that the ozone concentration is too high, the controller shuts off the ozone generation system 10 for a period of time. Preferably, the period of time is between one to ten seconds; however, other amounts of time may be selected. After the period of time, the controller 42 checks the ozone concentration again to determine whether the ozone concentration is in an acceptable range. If the ozone concentration is in the acceptable range, the controller 42 turns the ozone generation system 10 back on. In one construction, the first end 26 of the fiber optic cable 22 is positioned proximate the outlet 24 of the ozone generation system 10 to more closely determine the ozone concentration being released from the outlet 24.

In some constructions, the ozone generation system 10 is capable of operating some or all of the ROS generators 14 depending on the ozone concentration detected. For example, if the controller 42 determines that the ozone concentration is too low, the controller 42 operates all of the ROS generators 14. If the controller 42 determines that the ozone concentration is in the acceptable range, the controller 42 operates one or a portion of the ROS generators 14.

Figure 2:
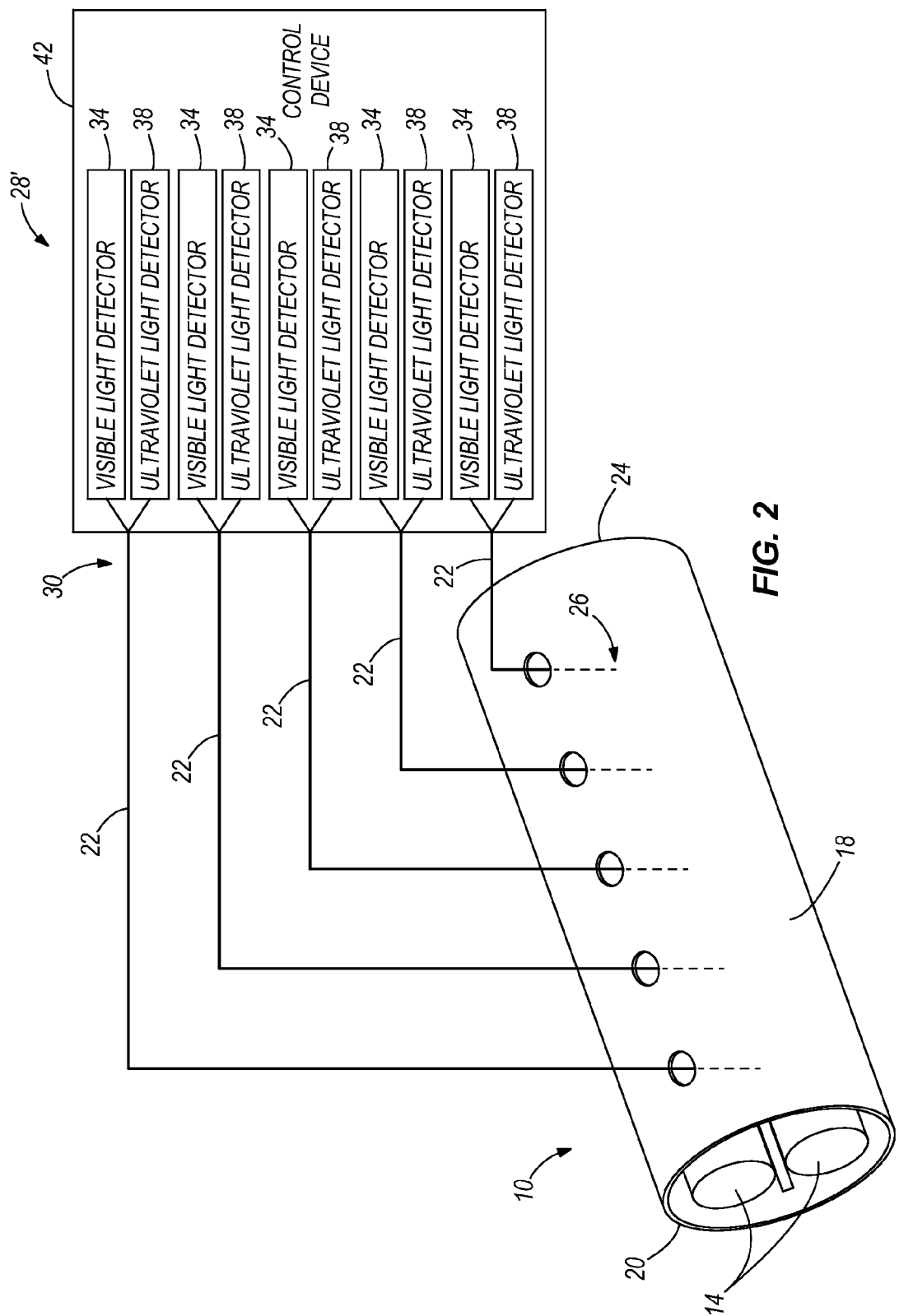
FIG. 2 is a schematic view of an ozone generator having a fiber optic detection system according to a second construction of the invention.

In another construction, illustrated in FIG. 2, multiple jacketed POF fiber optic cables 22 may be positioned at various locations along an axial length of the ROS generators 14. The control system of FIG. 2 will be denoted with the reference numeral 28'. The distribution of multiple fiber optic cables 22 improves the accuracy of the system because it is more likely that a cable 22 will be positioned in close proximity to a crack or failure in the ROS generators 14, thereby increasing the chances for the visible light detector 34 to detect a high amount of visible light corresponding to the failure. Each fiber optic cable 22 is associated with a visible light detector 34 and an ultraviolet light detector 38, as described above, and the ozone generation system 10 and control system 28' operate as described above. In other constructions, the fiber optic cables 22 may be positioned at various locations around the circumference of the ROS generator housing 18.

Figure 3:
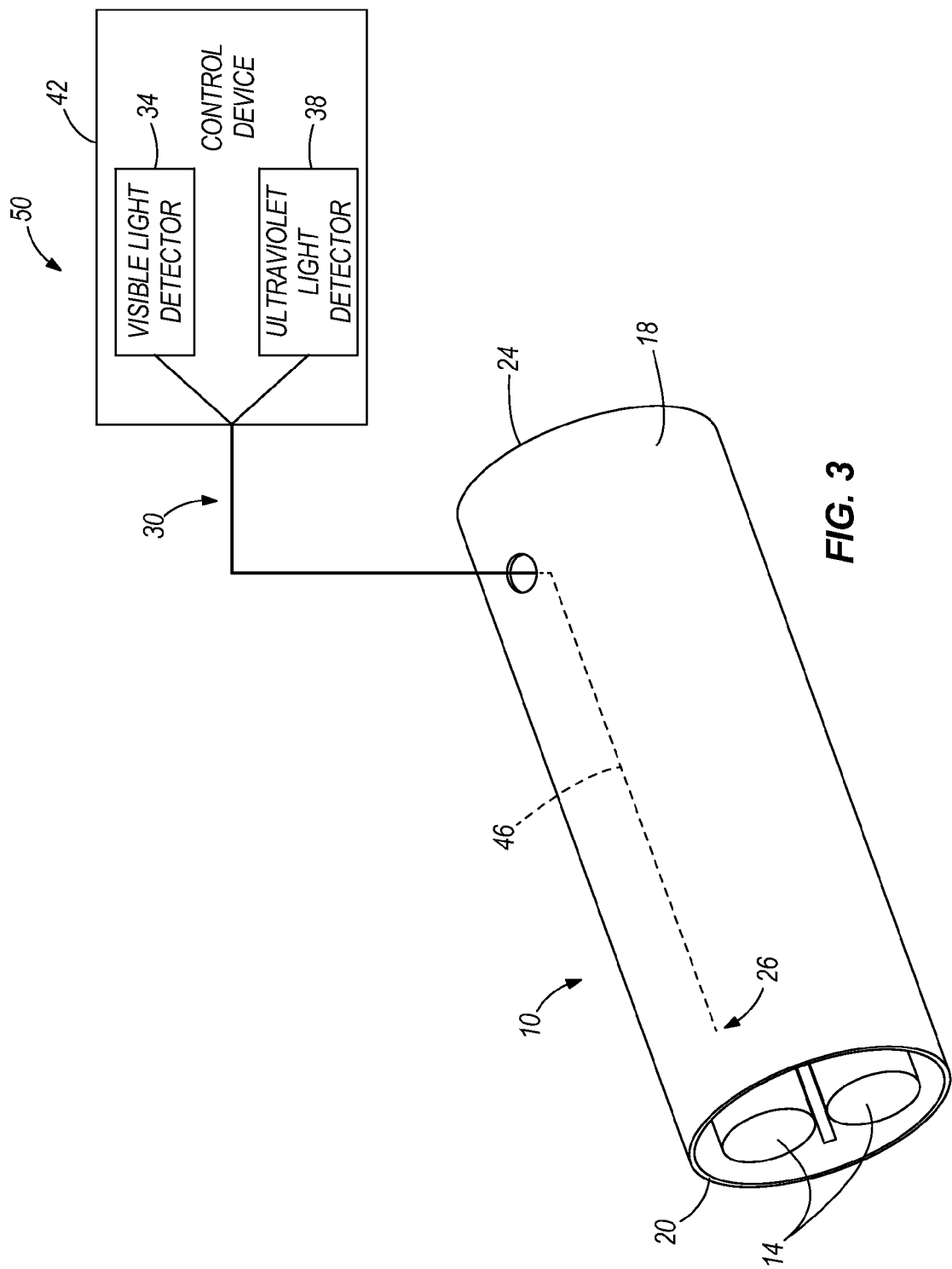
FIG. 3 is a schematic view of an ozone generator having a fiber optic detection system according to a third construction of the invention.

FIG. 3 illustrates another construction of a control system 50 including an unjacketed fiber optic cable 46, which does not include the polyethylene jacket on a length of cable positioned inside the housing 18. The unjacketed fiber optic cable 46 provides the same qualities as the jacketed POF fiber optic cable 22 except that light may be received along the unjacketed body of the fiber optic cable 46, as well as the ends 26, 30. This improves the accuracy of the system because it is more likely that the cable 46 will receive light in close proximity to a crack or failure in the ROS generators 14, thereby increasing the chances for the visible light detector 34 detecting a high amount of visible light corresponding to the failure. The control system 50 otherwise operates substantially the same way as the control system 28 illustrated in FIG. 1, and like features are labeled with the same reference numerals and operate in the same manner as described above. In other constructions, another unjacketed fiber optic cable could be positioned proximate another ozone generator tube 14; and in further constructions, one unjacketed fiber optic cable could be positioned proximate each ozone generator tube 14.

Figure 4:
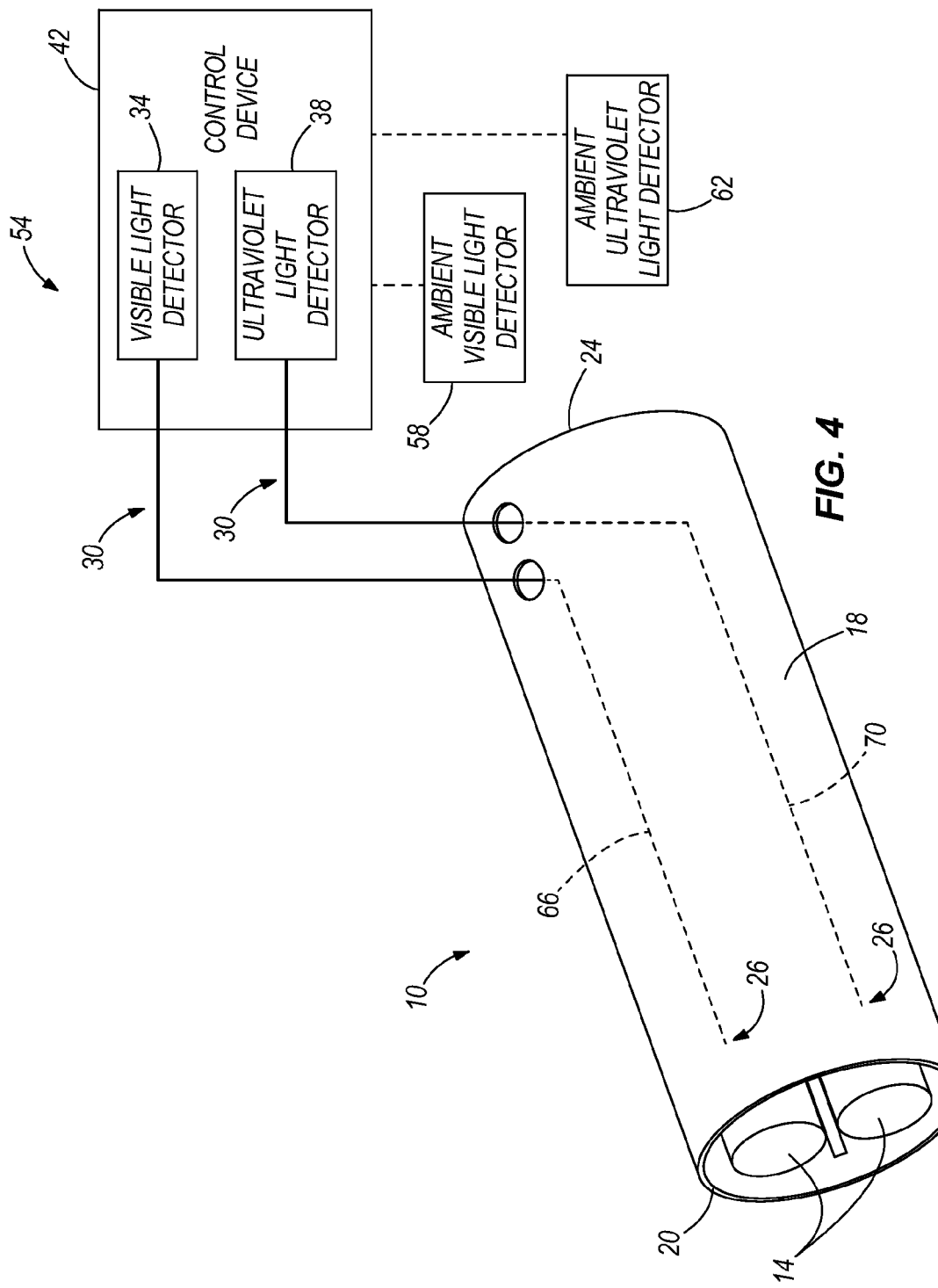
FIG. 4 is a schematic view of an ozone generator having a fiber optic detection system according to a fourth construction of the invention.

FIG. 4 illustrates another construction of a control system 54 having two unjacketed fiber optic cables 66, 70 operatively connected to the visible light detector 34 and the ultraviolet light detector 38, respectively. The control system 54 further includes an ambient visible light detector 58 and an ambient ultraviolet light detector 62. The light level detected by the visible light detector 58 is compared to the light level detected by the first unjacketed fiber optic cable 66 for calibration purposes. Dulling of the glass of the ROS generators 14 can cause changes in the light levels emitted therefrom. Using the ambient light level as a reference, the control system 54 can self-calibrate to compensate for changes in the glass. Similarly, the ultraviolet light detected by the ultraviolet light detector 62 can be compared to atmospheric ultraviolet light conditions for self-calibration of ozone generation within the ozone generation system 10. Any of the constructions of FIGS. 1-4 may include the ambient visible light sensor 58 and an ambient ultraviolet light sensor 62 as described above.

Figure 5:
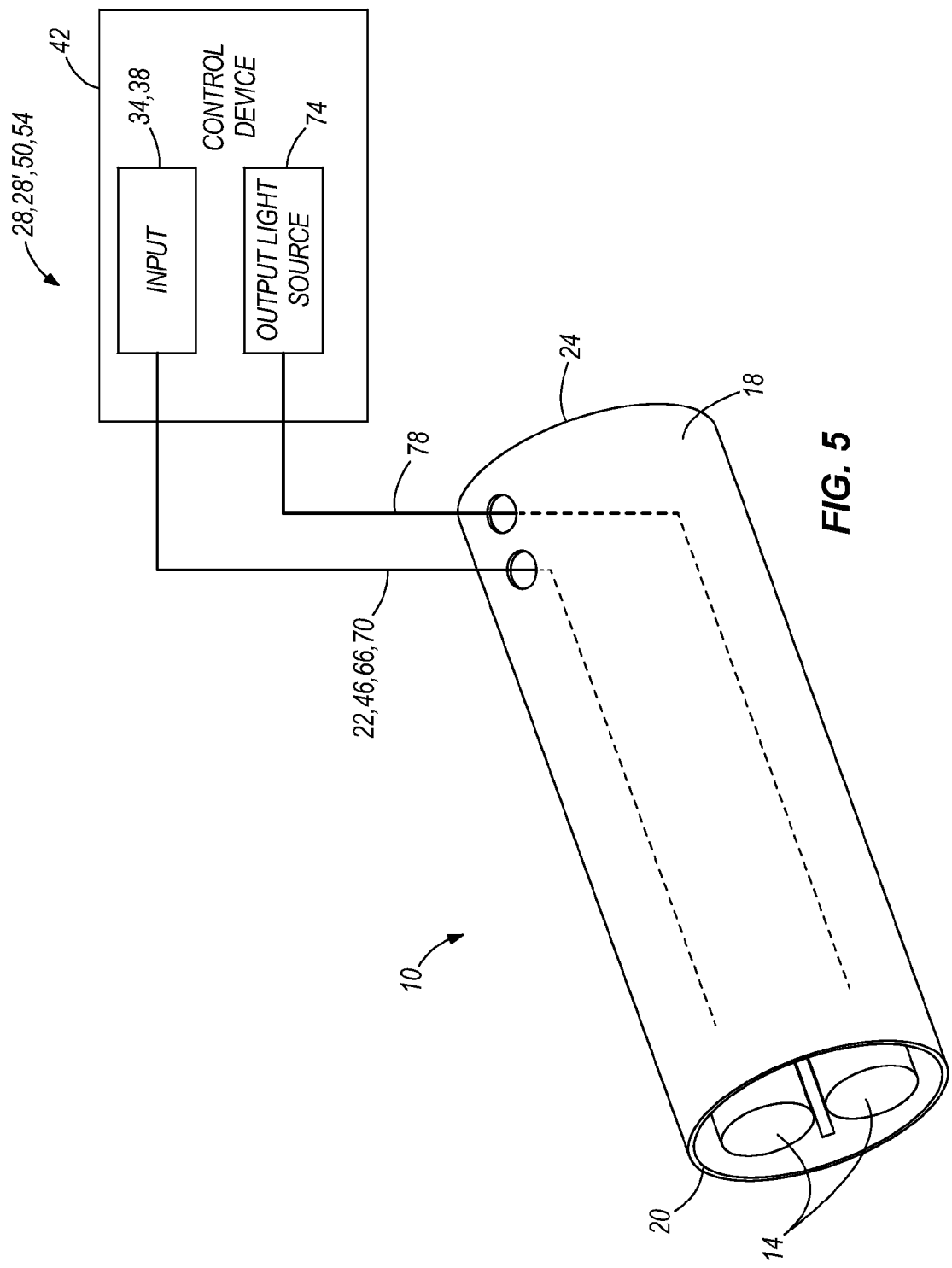
FIG. 5 is a schematic view of a self-test feature that may be employed with any of the ozone generators of FIGS. 1-4.

FIG. 5 illustrates an additional feature that may be employed with any of the constructions of FIGS. 1-4. An output light source 74 is coupled with an unjacketed fiber optic cable 78 that is similar to the unjacketed fiber optic cable 46 described above with respect to FIG. 3. Light from the output light source 74 is transmitted through the cable 78 and into the housing 18. Another fiber optic cable 22, 46, 66, 70, which could be any one or more of the fiber optic cables coupled to a light detector 34, 38 and described above, is positioned within the housing 18 for receiving the light within the housing 18. A diagnostic test can be performed on the other cable(s) 22, 46, 66, 70 by illuminating the output light source 74, transmitting the light into the housing 18 by way of the unjacketed fiber optic cable 78, and determining whether the light detector(s) 34, 38 receives the light from the light source 74. If the light is received, then the detector(s) 34, 38 is functioning properly.

In operation, the control system 28, 28', 50, 54 monitors an operational status of the ROS generators 14 as well as a concentration of ozone outputted by the ROS generators 14. One or more of the fiber optic cables 22, 46, 66 receives light from the ozone generators 14 and transmits the light to the visible light detector 34. The visible light detector 34 generates a signal corresponding to the amount of light detected. For example, a digital discrete method provides instantaneous detection of visible light above a predetermined level. This method may be used to turn the system 10 off in the event of a failure of one of the ROS generators 14. Analog linear methods provide constant monitoring of the actions of the ROS generators 14. Constant monitoring allows for real time failure detection via microprocessor and software control. Similarly, one or more of the fiber optic cables 22, 46, 70 transmit light to the ultraviolet light detector 38, which detects the optical absorption of ultraviolet light between 230 nanometers (nm) and 270 nm, and preferably at approximately 254 nm, to determine the concentration of ozone outputted by the ROS generators 14. The ultraviolet light detector 38 similarly generates a signal corresponding to the concentration of ozone. If the ozone concentration is too high, the ozone generation system 10 is shut down by the controller 42. The detectors 34, 38 can be calibrated using ambient sensors 58, 62 as reference points, respectively. Furthermore, diagnostic testing can be performed on the fiber optic cables 22, 46, 66, 70 and the detectors 34, 38 by transmitting a light source 74 into the housing 18 and determining whether the light source 74 is detected.

Thus, the invention provides, among other things, an air sanitization system utilizing fiber optic cables and light detectors for determining a functional status of ROS generators, and a method of controlling the air sanitization system to determine the functional status of the ROS generators. Various features and advantages of the invention are set forth in the following claims.

What is claimed is:
1. An air sanitization system comprising:
  a housing having an inlet and an outlet, the housing configured to receive a flow of an oxygen-containing gas through the inlet;
  an ozone generator disposed in the housing and positioned between the inlet and outlet, the ozone generator generating ozone from the flow of oxygen-containing gas;

at least one fiber optic cable positioned in visible proximity to the ozone generator and configured to receive and transmit visible light from the ozone generator;
a visible light detector for detecting an amount of visible light transmitted by the at least one fiber optic cable; and
a controller in communication with the visible light detector for determining whether the amount of visible light transmitted by the at least one fiber optic cable corresponds to a failure of the ozone generator.

2. The air sanitization system of claim 1, wherein the ozone generator includes at least one glass tube, and wherein failure of the ozone generator includes breakage of the at least one glass tube.

3. The air sanitization system of claim 1, wherein the ozone generator includes an array of glass tubes, and wherein failure of the ozone generator includes breakage of at least one of the glass tubes.

4. The air sanitization system of claim 1, wherein the controller is programmed to cease operation of the air sanitization system when a failure of the ozone generator is determined.

5. The air sanitization system of claim 1, further including at least one additional fiber optic cable positioned in visible proximity to the at least one fiber optic cable and configured to emit visible light from a light source to test the receiving and transmitting functions of the at least one fiber optic cable.

6. The air sanitization system of claim 1, wherein the at least one fiber optic cable includes an unjacketed portion positioned in visible proximity to the ozone generator and configured to receive visible light along a length of the unjacketed portion.

7. The air sanitization system of claim 1, wherein the at least one fiber optic cable includes a plurality of fiber optic cables positioned between the inlet and outlet for receiving and transmitting visible light from a plurality of locations between the inlet and outlet.

8. The air sanitization system of claim 1, further comprising:
at least one additional fiber optic cable positioned in visible proximity to the ozone generator and configured to receive and transmit ultra violet light from the ozone generator; and
an ultra violet light detector for detecting an amount of ultra violet light transmitted by the at least one additional fiber optic cable, wherein the ultra violet light detector is in communication with the controller for determining a level of ozone.

9. The air sanitization system of claim 8, wherein the ultra violet light detector detects optical absorption of ultra violet light between about 230 nm and about 270 nm.

10. The air sanitization system of claim 8, wherein the controller is programmed to control operation of the ozone generator dependent upon the level of ozone detected.

11. The air sanitization system of claim 8, wherein the at least one additional fiber optic cable is positioned proximate the outlet.

12. The air sanitization system of claim 1, further comprising an ambient light detector for detecting an amount of ambient light, the ambient light detector operatively coupled to the controller for calibration of the controller.

13. A method of controlling an air sanitization system, the method comprising:
generating ozone with an ozone generator;
positioning at least one fiber optic cable in visible proximity to the ozone generator to receive and transmit visible light from the ozone generator; positioning a visible light detector to detect an amount of visible light transmitted by the at least one fiber optic cable;
detecting visible light to determine failure of the ozone generator; and
ceasing operation of the ozone generator using a controller when a predetermined level of visible light corresponding to failure of the ozone generator is detected wherein said controller is configured to operate said ozone generator based on said detected visible light.

14. The method of claim 13, wherein detecting visible light includes detecting visible light within a housing of the ozone generator.

15. The method of claim 14, wherein detecting visible light further includes detecting visible light at a plurality of locations within the housing of the ozone generator.

16. The method of claim 13, further comprising transmitting visible light from the ozone generator to the visible light detector in communication with the controller.

17. The method of claim 13, further comprising emitting visible light, and testing whether the emitted visible light can be detected.

18. The method of claim 13, further comprising:
detecting ultra violet light to determine an amount of ozone generated by the ozone generator; and
controlling the ozone generator in response to the detected ultra violet light.

19. The method of claim 18, wherein detecting ultra violet light includes detecting optical absorption of ultra violet light between about 230 nm and about 270 nm.

20. The method of claim 13, further comprising calibrating the visible light detector by comparing an amount of visible light within a housing of the ozone generator to an amount of ambient visible light outside of the ozone generator.

21. An air sanitization system comprising:
a housing having an inlet and an outlet, the housing configured to receive a flow of an oxygen-containing gas through the inlet;
an ozone generator disposed in the housing and positioned between the inlet and outlet, the ozone generator generating ozone from the flow of oxygen-containing gas;
at least one fiber optic cable positioned in visible proximity to the ozone generator and configured to receive and transmit visible light from the ozone generator;
a visible light detector for detecting an amount of visible light transmitted by the at least one fiber optic cable;
at least one additional fiber optic cable positioned in visible proximity to the ozone generator and configured to receive and transmit ultra violet light from the ozone generator;
an ultra violet light detector for detecting an amount of ultra violet light transmitted by the at least one additional fiber optic cable; and
a controller in communication with the visible light detector for determining whether the amount of visible light transmitted by the at least one fiber optic cable corresponds to a failure of the ozone generator, the controller also being in communication with the ultra violet light detector for determining a level of ozone and for controlling operation of the ozone generator dependent upon the level of ozone detected,
wherein the controller is programmed to cease operation of the air sanitization system when a failure of the ozone generator is determined.

\* \* \* \* \*